(12) United States Patent
Greiner-Perth et al.

(10) Patent No.: US 9,375,538 B2
(45) Date of Patent: Jun. 28, 2016

(54) MEDIA DISPENSER

(71) Applicants: Juergen Greiner-Perth, Gottmadingen (DE); Peter Koenig, Rielasingen-Worblingen (DE); Nicole Schwarz, Radolfzell (DE)

(72) Inventors: Juergen Greiner-Perth, Gottmadingen (DE); Peter Koenig, Rielasingen-Worblingen (DE); Nicole Schwarz, Radolfzell (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 50 days.

(21) Appl. No.: 14/372,392

(22) PCT Filed: Nov. 21, 2012

(86) PCT No.: PCT/EP2012/073210
§ 371 (c)(1),
(2) Date: Jul. 15, 2014

(87) PCT Pub. No.: WO2013/107541
PCT Pub. Date: Jul. 25, 2013

(65) Prior Publication Data
US 2015/0014368 A1 Jan. 15, 2015

(30) Foreign Application Priority Data
Jan. 16, 2012 (DE) .......... 10 2012 200 545

(51) Int. Cl.
*B65D 83/00* (2006.01)
*A61M 11/00* (2006.01)
(Continued)

(52) U.S. Cl.
CPC .............. *A61M 11/007* (2014.02); *A45D 34/04* (2013.01); *A61M 15/009* (2013.01); *A61M 15/08* (2013.01);
(Continued)

(58) Field of Classification Search
CPC . A61M 11/007; A61M 15/009; A61M 15/08; B65D 83/201; B65D 83/206; A45D 34/04; A45D 2200/057; B05B 15/065
USPC .................... 222/402.1–402.25, 321.7–321.9
See application file for complete search history.

(56) References Cited

U.S. PATENT DOCUMENTS 3,518,410 A 6/1970 Dillarstone
3,596,056 A 7/1971 Dillarstone
(Continued)

FOREIGN PATENT DOCUMENTS

FR 2 900 645 A1 11/2007
GB 1 221 191 A 2/1971
(Continued)

OTHER PUBLICATIONS

Office Action of European Patent Office issued in Application No. 12 788 537.4 dated May 29, 2015 (4 pages).
(Continued)

*Primary Examiner* — Lien Ngo
(74) *Attorney, Agent, or Firm* — Flynn, Thiel, Boutell & Tanis, P.C.

(57) ABSTRACT

Dispenser for the delivery of liquid media, having a base unit and a delivery head with a delivery opening. The delivery head includes a first portion which includes a fastening device by means of which the first portion is fastened or fixed in position with respect to a media storage unit on the base unit, and which includes the delivery opening. The delivery head includes a second portion realized so as to be movable in relation to the first portion and includes an actuating handle which is operatively coupled with the coupling piece such that a displacement of the actuating handle in relation to the first portion leads to a displacement of the coupling piece in relation to the first part portion.

12 Claims, 11 Drawing Sheets

(51) Int. Cl.
*A45D 34/04* (2006.01)
*B65D 83/20* (2006.01)
*A61M 15/00* (2006.01)
*A61M 15/08* (2006.01)
*B05B 15/06* (2006.01)

(52) U.S. Cl.
CPC ............ *B65D 83/201* (2013.01); *B65D 83/206* (2013.01); *A45D 2200/057* (2013.01); *B05B 15/065* (2013.01)

(56) References Cited

U.S. PATENT DOCUMENTS

| | | | |
|---|---|---|---|
| 4,187,963 A * | 2/1980 | Mascia | B65D 83/205 222/402.13 |
| 5,617,978 A * | 4/1997 | Geier | B65D 83/205 222/153.06 |
| 6,089,410 A | 7/2000 | Ponton | |
| 6,543,653 B2 | 4/2003 | Lamboux | |
| 7,582,242 B2 | 9/2009 | Kolanus | |
| 7,789,278 B2 * | 9/2010 | Ruiz de Gopegui | B05B 7/2435 222/136 |
| 7,886,939 B2 | 2/2011 | Michaux | |
| 8,863,995 B2 | 10/2014 | Stegeman | |
| 2002/0134798 A1 | 9/2002 | Lamboux | |
| 2004/0112924 A1 * | 6/2004 | Albisetti | B65D 83/206 222/402.13 |
| 2007/0257067 A1 | 11/2007 | Parmentier et al. | |
| 2009/0045223 A1 | 2/2009 | Laidler et al. | |
| 2009/0050650 A1 * | 2/2009 | Walters | B65D 83/205 222/153.11 |
| 2009/0314810 A1 * | 12/2009 | Neuhaus | B05B 11/007 222/402.13 |
| 2010/0147898 A1 * | 6/2010 | Blumenstein | B05B 11/0027 222/402.13 |
| 2010/0200616 A1 * | 8/2010 | Decottignies | B05B 11/007 222/207 |

FOREIGN PATENT DOCUMENTS

| | | |
|---|---|---|
| WO | WO 01/25116 A1 | 4/2001 |
| WO | WO 01/44076 A2 | 6/2001 |
| WO | WO 2006/013353 A1 | 2/2006 |
| WO | WO 2012/100014 A1 | 7/2012 |
| WO | WO 2013/023019 A1 | 2/2013 |

OTHER PUBLICATIONS

Examination Report of German Patent Office issued in German Application No. 10 2012 200 545.5 dated Jun. 27, 2012 (6 pages).
Form PCT/ISA/210 International Search Report issued in International Application No. PCT/EP2012/073210, date of mailing Feb. 25, 2013 (6 pages).

* cited by examiner

Fig. 10a Fig. 10b

MEDIA DISPENSER

FIELD OF APPLICATION AND PRIOR ART

The invention relates to a dispenser for the delivery in particular of liquid media, said dispenser having a base unit and a delivery head. In this case, the base unit includes a media storage unit, which is realized for storing a medium, and an outlet connecting piece which is movable in relation to the media storage unit for the purpose of the delivery of a medium in the direction of the delivery head through the outlet connecting piece. The named delivery head comprises a delivery opening, through which the medium is able to escape into a surrounding atmosphere. Over and above this, it comprises a delivery channel, on the first end of which there is provided a coupling piece for coupling to the outlet connecting piece and the second end of which is connected to the delivery opening.

Generic dispensers are known in general from the prior art. In the case of generic dispensers, there are provided the two named part units, the base unit and the delivery head, which are connected together during the course of the assembly of the dispenser. For this purpose, the delivery head is coupled with the base unit in such a manner that once successfully coupled, the outlet connecting piece of the base unit is able to be moved by means of a movement of the delivery head.

Although many known dispensers fulfill the named features of a generic dispenser, the invention relates in particular to such generic dispensers where the media storage unit of the base unit is provided for storing a permanently pressurized medium and where the movement of the outlet connecting piece in relation to the media storage unit causes the opening of an outlet valve such that the medium is able to flow through the outlet connecting piece out of the medium storage unit. Such generic dispensers are generally known, for example, in the form of deodorant dispensers.

Along with dispensers from the area of body hygiene or cosmetics, the invention also relates in particular, however, to generic dispensers for discharging pharmaceutical media. Thus, generic dispensers are also distributed as nasal spray dispensers.

In particular in the case of said nasal spray dispensers, however also in the case of other generic dispensers, it is deemed to be disadvantageous for the delivery head to be displaced usually in its entirety or at least together with the delivery opening for the delivery of a medium. This makes it more difficult to deliver the medium in a targeted manner.

OBJECT AND SOLUTION

It is the object of the invention to develop further a generic dispenser to the effect that said dispenser allows a more precise targeted delivery of the medium, an object of the invention over and above this being in particular to indicate ways in order to develop such a dispenser according to the invention in a manner that is simple to assemble.

The object underlying the invention is achieved in that the named delivery head comprises a first part portion which comprises a fastening device, by means of which it is fastened fixed in position with respect to the media storage unit on the base unit and which also includes the delivery opening. It additionally comprises according to the invention a second part portion which is realized so as to be movable in relation to the first part portion and comprises an actuating handle which is operatively coupled with the coupling piece in such a manner that a displacement of the actuating handle in relation to the first part portion leads to a displacement of the coupling piece in relation to the first part portion.

In the case of a dispenser according to the invention, it is consequently provided that the delivery head includes part portions which are displaceable in relation to one another. A first part portion is provided for the fixed attachment in relation to the media dispenser such that, when used as intended, it is not moved in relation to the media storage unit. For this purpose, the first part portion is preferably realized in the manner of a hood which is connected to the base unit in the region of a circumferential edge and covers the end of the base unit pointing in the direction of the delivery head, the fastening being effected on the named edge, for example, by snap-hooks or the like which engage in indentations on the base unit.

The first part portion also includes the delivery opening such that this also remains fixed in position with respect to the media storage unit of the base unit. As a dispenser according to the invention is held and guided by the user/patient preferably on the media storage unit, the delivery opening which is fixed with respect hereto can accordingly be positioned correctly in a simple manner.

A second part portion of the delivery head is realized so as to be movable in relation to the first part portion and has an actuating handle which is provided for manual actuation. As a result of the displacement of said second part portion in relation to the first part portion, a displacement of the coupling piece in relation to the first part portion can also be caused, which, in turn, allows the medium to flow out of the media dispenser. In the simplest case, the actuating handle and the coupling piece are coupled with one another in such a manner that they remain fixed with respect to one another such that the coupling piece and consequently the outlet connecting piece are always displaced to the same extent as the actuating handle. It is, however, also possible for a different operative coupling to be realized, as will be explained further below.

The outlet connecting piece does not have to be engaged around by the coupling piece. A displaceable ring into which as the female component the coupling piece is inserted is also to be understood as an outlet connecting piece in terms of the invention.

A dispenser according to the invention can be realized in a variety of ways. Thus, for example, a pump device, which conveys the medium as a result of displacement of the outlet connecting piece in relation to the media storage unit, can be part of the base unit.

A configuration where the media storage unit is realized for storing over-pressurized medium and/or is filled with over-pressurized medium, however, is preferred. The outlet connecting piece of the base unit of such a dispenser is connected in such a manner to an outlet valve which is provided in the base unit that a displacement of the outlet connecting piece in relation to the media storage unit leads to an opening of the outlet valve. The medium flows through the outlet connecting piece in reaction to said opening of the outlet valve.

The outlet connecting piece is movable in relation to the base unit preferably in a straight line in the main direction of extension of the dispenser. In the individual case, however, it can be tiltable or relatively movable in another manner. Precisely in conjunction with dispensers with the named specific development of the base unit with a pressurized medium, it has been current practice up to now for the delivery head to be developed in the above-described manner such that the delivery opening is moved in relation to the media storage unit when the actuating handle is manually actuated. This is avoided according to the invention.

The delivery head of a dispenser according to the invention, which comprises the delivery opening, is preferably realized in such a manner that the delivery direction at the delivery opening encloses an angle in excess of 0° and less than 30°, preferably an angle of between 5° and 15°, with the named main extension direction of the dispenser. In addition, it is seen as advantageous when the delivery opening is arranged eccentrically on the delivery head, that is not in alignment with the outlet connecting piece.

So that the medium can pass from the outlet connecting piece and the coupling piece connected hereto to the delivery opening, the already mentioned outlet channel is provided. As in the case of a dispenser according to the invention, the coupling piece and the delivery opening are displaced in relation to one another during the course of the actuation of the actuating handle, the shaping of said outlet channel must be modifiable. It is deemed to be a particularly simple configuration for this purpose when the outlet channel between the coupling piece and the delivery opening is formed at least in portions by a flexible-form hose portion. The end of said hose portion which points to the delivery opening remains fixed in position with respect to the first part portion, whilst the opposite end of the hose portion remains fixed in position with respect to the coupling piece. The hose portion can be realized as a separate component. However, it can also be realized integrally with one of the adjacent components, for example the coupling piece.

In the simplest case, the hose portion is realized with a uniform inside and outside cross section. In order to reduce or to influence the buckling tendency of the hose, it can, however, be advantageous when the hose portion comprises a non-uniform inside or outside cross section over its length. As a result it is possible to prevent local narrowing of the inside cross section of the hose portion which obstructs the media delivery. Particularly advantageous is a development where the outside cross section comprises several widenings, for example in the form of circumferential webs which, when the hose bends, come into contact with one another and as a result prevent more extensive bending. A similar effect can be achieved as a result of tangentially aligned notches.

Maximum deformability in the region of two adjacent widenings is defined as a result of the widenings. This does not totally prevent deformability going beyond this when there is simultaneous unwanted kinking of the hose. However, a correspondingly developed hose ensures that prior to continued deformation in one part portion of the hose, deformation in other part portions of the hose takes place first of all such that total closing of the delivery channel is prevented.

An alternative to a flexible hose portion is provided in the case of a preferred development of a dispenser according to the invention in that the delivery channel between the outlet connecting piece and the coupling piece on the one hand and the delivery opening on the other hand is formed at least in part by a telescopic channel region. In the region of the telescopic channel region there are provided two channel portions which are displaceable in relation to one another, one of which by fitting into the other enables a variable length of the telescopic channel region. The two channel portions, in this case, are in contact with one another circumferentially in order to achieve effective sealing of the channel in relation to a surrounding area.

The telescopic channel region is preferably aligned in the main extension direction of the dispenser. Where a base unit includes an outlet connecting piece which is displaceable in a straight line, the telescopic channel region is preferably telescopic parallel to the direction of displacement of the outlet connecting piece.

A solution for achieving the variability in form of the delivery channel which is also deemed to be advantageous provides that said delivery channel is formed in part by an inside tube and a sleeve which is displaceable on the outside of the inside tube, both the inside tube and the sleeve comprising an opening through which medium is able to flow in the direction of the delivery opening. In this case, the openings are preferably to be provided with a sufficient size as a result of which a permanent connection between a channel portion, which connects to the sleeve, and the interior of the inside tube is provided.

In principle, in the case of a dispenser according to the invention, it is possible to have a configuration where the second part portion, which includes the actuating handle, always remains fixed in position with respect to the coupling piece. In such a case, the guiding of the second part unit on the first part unit at the same time provides guiding for the coupling piece.

However, a configuration is preferred where there is no permanent immobility between the second part unit and the coupling piece, provided for example as a result of integrality or a fixed connection. In such a case, it is advantageous when guiding for the coupling piece is nevertheless provided.

A configuration of such guiding provides that on the side of the base unit which points to the delivery head there is provided a cover which closes a cylindrical outside wall of the base unit at the end, said cover defining a guiding face on which guiding portions which are fixedly connected to the coupling piece are sliding movable.

The named cover can preferably be a crimp cover which closes the approximately cylindrical media storage unit of the base unit at the end. The cover makes available the named guiding face, corresponding to which the forming of guiding portions of the coupling piece is effected. In the assembled state, the coupling piece is consequently movable in a guided manner by the guiding face and the guiding portions connected thereto, in particular movable in a straight line in a guided manner. The guiding face on the cover side can preferably be a cylindrical guiding face, it being possible for it to be both an inside cylindrical and an outside cylindrical face against which the guiding portions abut. In principle, the guiding face can also comprise a form that deviates from the cylindrical form, in this case guiding portions which allow for corresponding deformability being necessary on the part of the coupling piece.

The named guiding of the coupling piece on the cover of the base unit does make the desired guiding of the coupling piece available in operation. However, it can only serve to a limited extent for positioning the coupling piece during the assembly of the dispenser.

A configuration which is advantageous in this respect provides that the dispenser comprises a guiding device which is realized completely in the delivery head and is realized for the purpose of enabling a movement of the coupling piece in relation to the first part portion only along a defined case of movement. Such a guiding device realized completely in the delivery head leads to desired positioning of the coupling piece even prior to the coupling of the delivery head to the base unit. As a result, the assembly is made easier as no separate measures are necessary in order to position the coupling piece in alignment with the outlet connecting piece.

The guiding device, in this case, is preferably realized as a slip-in guide with at least two slip-in guide portions which are adapted to one another and are displaceable in a linear manner in relation to one another. In the case of a preferred configuration, a plurality of spokes, which are connected either fixedly to the first part portion or fixedly to the coupling piece and which are guided at the end into grooves on the coupling piece or on the first part portion, extend between the first part portion of the delivery head which surrounds the coupling piece and the coupling portion.

For positioning the coupling piece even prior to assembly of the delivery head on the base unit, another advantageous development provides that there is provided at least one, preferably at least two deformable bridges which are connected at the one end to the coupling piece and which are held at the other end fixed in position with respect to the first part portion of the delivery head. Said bridges consequently comprise in each case one end which remains fixed in position in relation to the coupling piece, for example as a result of integral development. The respective opposite other bridge end remains fixed in position with respect to the first part portion, for example by being integrally realized with said first part portion or by being connected to a holding portion, such as a holding ring which is fastened in a fixed position with respect to the first part portion. Such deformable bridges, which, as a result of their deformability, allow the relative movement of the coupling piece in relation to the first part portion, can also ensure during assembly the positioning of the coupling piece and consequently the simplicity of the assembly. Several bridges which extend radially from the outside to the coupling piece are preferably provided.

As already mentioned, it is preferably provided in the case of the delivery head of a dispenser according to the invention that there is no fixed connection between the second part portion and the coupling piece such that the movement path of the coupling piece in relation to the first part portion does not have to correspond with the movement path of the second part portion with the actuating handle in relation to the first part portion. The operative coupling between the displacement of the second part portion in relation to the first part portion on the one hand and the displacement of the coupling piece in relation to the first part portion on the other hand is preferably also effected at least by means of a pivot lever which is mounted so as to be pivotable on the first part portion and which can be pivoted as a result of displacement of the second part portion in relation to the first part portion. Said pivot lever is operatively coupled in such a manner with the coupling piece that the pivoting movement of the pivot lever also brings about the displacement of the coupling piece.

The use of such a pivot lever offers a plurality of advantages. In particular, it allows for a comparably flexible arrangement of the second part portion as said second part portion no longer has to align at least approximately with the outlet connecting piece and the first coupling piece. Over and above this, it can be achieved that a comparatively wide movement of the second part portion is required in order to bring about the mostly only small movement of the coupling piece which is necessary for the purposes of the media delivery. The delivery operation can be metered well in this manner.

The pivot lever can be realized as a separate component which is fastened on the first part portion as a result of hinging means. An integral configuration with a film hinge is also conceivable.

Along with the named advantages, the use of a pivot lever can also be advantageous in order to bring about the desired positioning and/or guiding of the coupling piece. For this purpose, the coupling piece can be fastened in a fixed or pivotable manner on the pivot lever. A coupling of this type does result in the coupling piece not being linearly movable corresponding to the mobility of the pivot lever. Even in the case of a configuration of the base unit with a linearly movable outlet connecting piece, however, this does not pose any problem as the pivot lever is preferably pivoted about no more than a maximum of 20°. Where the pivot axis is arranged in a suitable manner, the displacement of the coupling piece transversely with respect to the direction of movement of the outlet connecting piece is consequently negligibly small.

In principle, the second part portion of the dispenser just as the first part portion can be produced from a comparably rigid plastics material. In this case, a slip-in guide is preferably provided between the two part portions. A preferred configuration, however, provides that the second part portion consists at least in part of an elastically deformable material (modulus of elasticity<0.5 kN/mm$^2$), on account of which the actuating handle is movable in relation to the first part portion. The second part portion is preferably produced in its entirety from said material. In addition, the second part portion is preferably connected fixedly to the first part portion in edge regions and consequently is not movable in edge regions in relation to the same. The production of such a delivery head with a second part portion of elastically deformable material is preferably effected by means of two component injection molding such that the first and the second part portions are connected together in an integral manner.

The operative coupling between the coupling piece and the second part portion can be in such a manner that the displacement or deforming of the second part portion leads to an application of force of a portion which is operatively coupled with the coupling piece or is connected to the same without a permanent connection between the second part portion and the named coupling piece portion being necessary. However, it is deemed to be advantageous when there is provided a fastening portion which is provided so as to be fixed in position with respect to the coupling piece and is connected in a non-positive locking, positive locking or positively bonded manner to the elastically deformable material of the second part portion. A positioning of the coupling piece for the purpose of simplified assembly can also be achieved as a result. In particular, a recess into which an insertion portion of the fastening portion projects can be situated in the elastically deformable material.

In order to displace the coupling piece during the course of an actuation of the actuating handle and of a movement of the second part portion in relation to the first part portion which accompanies it, said coupling piece preferably has at least one pressing face. In this case, it can be provided in the case of a preferred development that the at least one pressing face is arranged radially offset with respect to the outlet connecting piece. With reference to the main extension direction, the pressing face is consequently not aligned with the outlet connecting piece in the case of such a configuration. As a result it is possible, without impairing the course of the outlet channel between the coupling piece and the delivery opening, to bring about the application of force of the coupling piece which is necessary for the purpose of a delivery operation. However, it is also conceivable to arrange the pressing face in alignment with the outlet connecting piece, in this case the delivery channel being deflected in the region of the coupling piece and below the pressing face such that it is guided past the side of the pressing face which is in alignment with the outlet connecting piece.

The invention additionally relates, in particular as a further development of the configuration described, to a dispenser for media which has a media storage unit which is realized for storing a medium, in particular a liquid, a delivery opening through which a medium is able to be discharged into a surrounding atmosphere and a delivery channel which connects the media storage unit to the outlet opening, the delivery channel being defined at least in portions by two plastics material components, which are realized integrally together as a result of two-component injection molding, from different plastics material, of which the softer plastics material comprises a maximum modulus of elasticity of 0.3 kN/mm². Of the two plastics material parts from that plastics material, one is produced from the named soft plastics material with a maximum modulus of elasticity of 0.3 kN/mm², whilst the other is preferably produced from a clearly more rigid plastics material, in particular a plastics material with a modulus of elasticity of at least 1 kN/mm². In order to prevent the delivery channel closing in spite of the two component injection molding, the component consisting of the more rigid plastics material is preferably produced first of all and then treated with a coating or radiation exposure in the region of the subsequent delivery channel in order to prevent positive bonding being produced between the two plastics material components in said region when the softer component is injected.

The named at least portionwise forming of the delivery channel as a result of the two plastics material components being connected together using two component injection molding offers many advantages. As a result, a delivery channel which fulfills a valve function at the same time, for example, can be created in a simple manner in this way.

In addition, when the plastics material component of softer plastics material is provided at least in portions on the outside surface of the dispenser, this can at the same time form the actuating handle. Along with the fact that a dispenser according to the invention can be produced with a smaller number of components as a result, said configuration is also advantageous consequently as it also allows the media delivery to be made recognizable in a haptic manner in the region of the actuating handle. As a result of the widening of the outlet channel which takes places during delivery, the operator can feel that the delivery is taking place.

BRIEF DESCRIPTION OF THE DRAWINGS

Further aspects and advantages of the invention are produced apart from the claims also from the following description of preferred exemplary embodiments of the invention. The drawings are as follows:

DETAILED DESCRIPTION OF THE EXEMPLARY EMBODIMENTS

Figure 1:
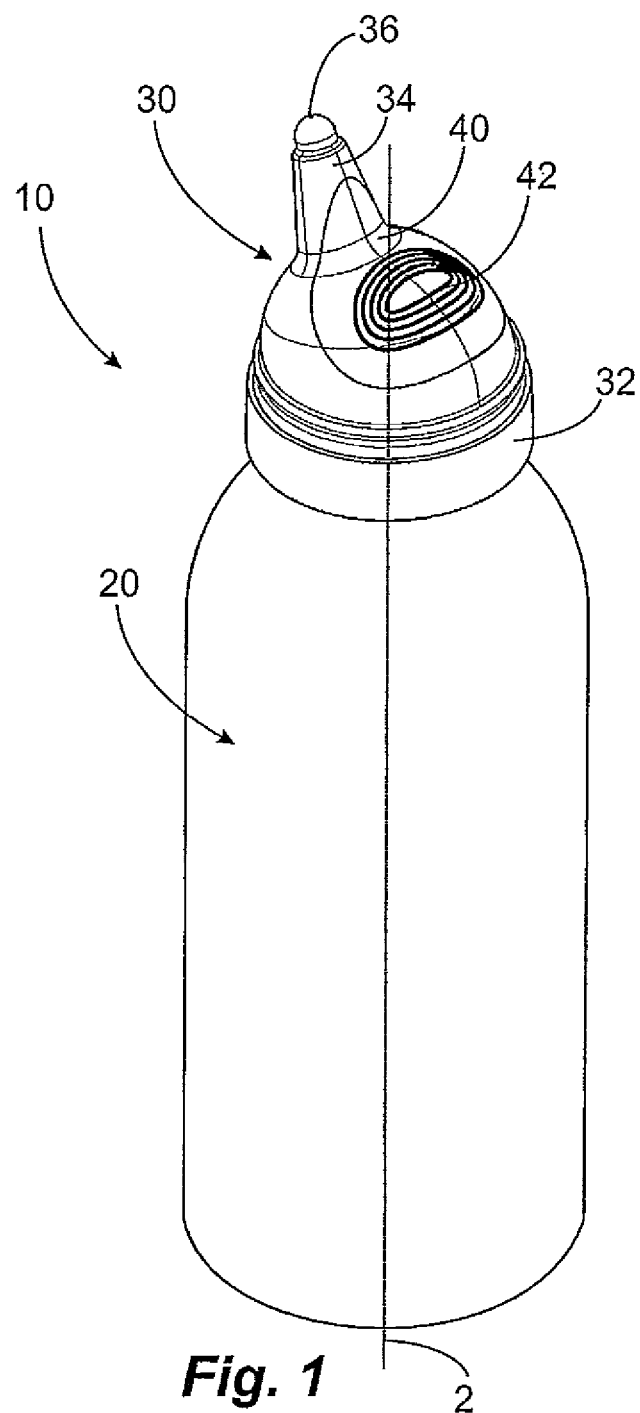
FIG. 1 shows the basic design of a dispenser according to the invention.

FIG. 1 shows the basic design of a dispenser according to the invention. The basic design of the dispenser, which is at least extensively identical for all the developments according to the invention described here, is explained initially by way of said figure as well as by way of the first exemplary embodiment of FIGS. 2a and 2b which is more precise with regard to the delivery head of said dispenser.

The dispenser 10 according to the invention has a base unit 20 and a delivery head 30 which is placed thereon. The base unit 20 is formed predominantly by a media storage unit 22 which in the case of the exemplary embodiments is surrounded by a pressure container 24 which is rotationally symmetrical with respect to a main extension axis 2. At the top end face of the pressure container 24, the same is closed by means of a crimp cover 26. The crimp cover 26, in turn, comprises centrally an opening 26a through which an outlet connecting piece 28a projects through an outlet valve unit 28. The outlet connecting piece 28a is displaceable in the direction of the arrow 2a against the force of a valve spring (not shown) of the outlet valve unit 28, an opening of the valve unit 28 and consequently an emerging of the liquid out of the liquid storage unit 22 being made possible as a result of a displacement of this type. The outlet connecting piece 28a is hollow and cylindrical. The medium emerging out of the media storage unit 22 flows through the outlet connecting piece 28a.

The already mentioned delivery head 30 is placed onto the base unit 20. Said delivery head 30 has a first part portion 32 which is fixed in position with respect to the pressure body 24 and forms the predominant part of the delivery head 30. Along with a fastening device 37 for the purpose of fastening the first part portion 32 on the pressure body 24, the first part portion 32 also includes the delivery opening 36, through which the medium, in particular a liquid in the form of spray streams, is able to be delivered into a surrounding atmosphere. The delivery opening, in the case of the dispenser 10 provided in the exemplary embodiments, is provided on the distal end of a conical nasal applicator 34 which is arranged angled at an angle of approximately between 10° and 15° in relation to the main extension axis 2 of the dispenser 10 and inside which is provided an insert 35 which is fixed in position with respect to the applicator 34.

The delivery head 30 has over and above this a second part portion 40 which is movable in a relative manner in relation to the first part portion 32. In the case of the present exemplary embodiments, said second part portion is formed at least in part by a component of a comparatively soft and consequently deformable thermoplastic plastics material, which is fastened in edge regions on the first part portion 32, for example is connected to said first part portion as a result of two-component injection molding. The second part portion 40, which is movable in relation to the first part portion 32 and the pressure container 24, is also carrier of an actuating handle 42 which can be pressed down for the purpose of the delivery of a medium.

The development shown with integrality between the first part portion and the second part portion or the actuating handle can also be replaced by a configuration where the second part portion is configured completely separately and said second part portion is movable in a guided manner in relation to the first part portion.

The handling of the dispenser according to the invention is effected in such a manner that the delivery opening 36 is positioned in the desired delivery position. The actuating handle 42 is then pressed down in relation to the pressure body 24, which serves at the same time for holding the dispenser 10. As a result, a liquid delivery is brought about, this not being accompanied by a displacement of the delivery opening 36 in relation to the pressure container 24. Said immobility of the delivery opening 36 in relation to the pressure container 24 is advantageous in the case of many applications, for example when using a dispenser 10 utilized as a nasal spray dispenser where the immobility prevents the applicator 34 from undergoing displacement during the course of the actuation inside a nostril of the user.

Different developments of the delivery head are explained below. In the case of said embodiments, different integral components are provided in each case. Insofar as in the case of the embodiments different part portions of a component are realized fixed in position with respect to one another as a result of integrality, this is, however, to be understood simply as an example. The corresponding components can also be formed in multiple parts by part components which are connected together.

Figure 2A:
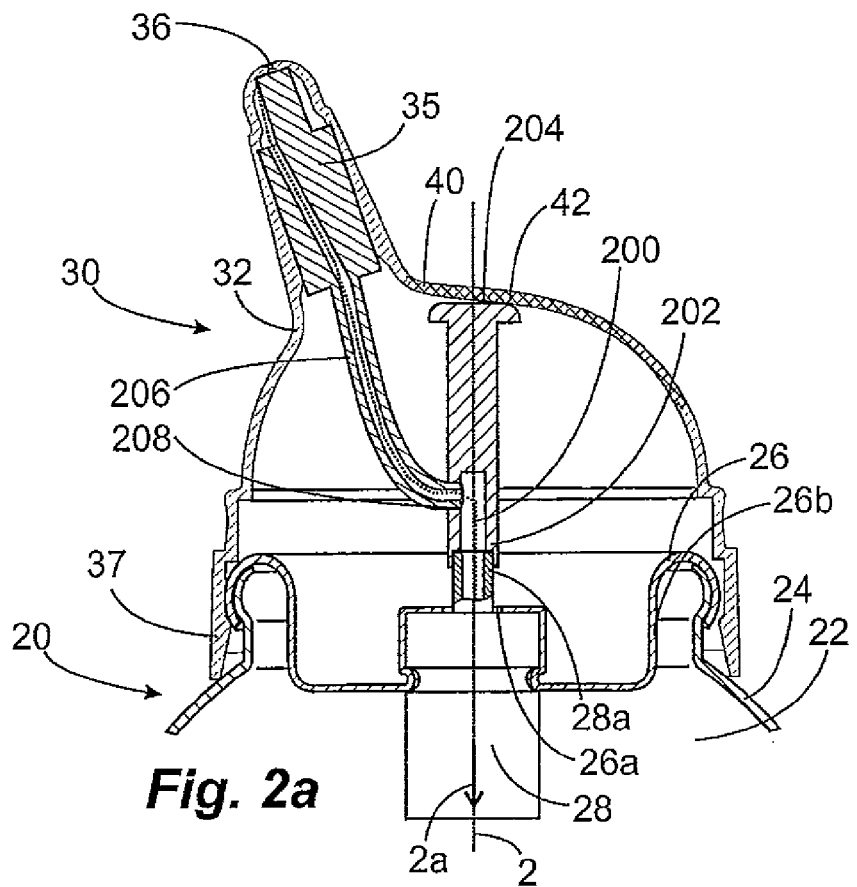
FIGS. 2 to 12 show a total of eleven variations of the delivery head of a dispenser according to the invention.
Figure 2B:
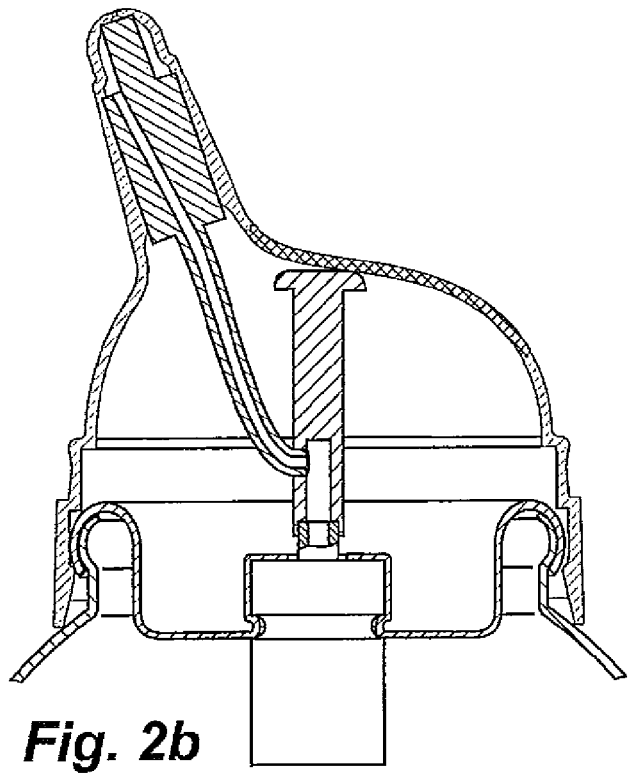

In the case of the development according to FIGS. 2a and 2b, there is provided a coupling piece 202 which is placed onto the outlet connecting piece 28a. Said coupling piece comprises on its end opposite the outlet connecting piece 28a a pressure applying face 204 which is arranged below the second part portion 40 and, as a result of pressing down the second part portion 40 or the actuating handle 42 provided thereon, can be displaced downward also in the direction of the arrow 2a. The coupling piece 202, in this case, is realized in a hollow manner in a bottom region and comprises a coupling bore 208 which extends radially outward and into which a variable-form hose portion 206 is inserted. In the case of an alternative development, the hose portion 206 can also be realized integrally with the coupling piece 202. The opposite end of the hose portion 206 ends at the fill piece 35 which is arranged fixed in position inside the applicator 34. The fill piece 35 is provided with a bore, which is part of the delivery channel 200, through which the medium is able to pass from the outlet connecting piece 28a as far as up to the delivery opening 36. As FIG. 2b illustrates, no direct and permanent coupling between the second part portion 40 and the coupling piece 202 is required in order to be able to bring about the displacement of the coupling piece 202 by means of the actuating handle 42.

Figure 3A:
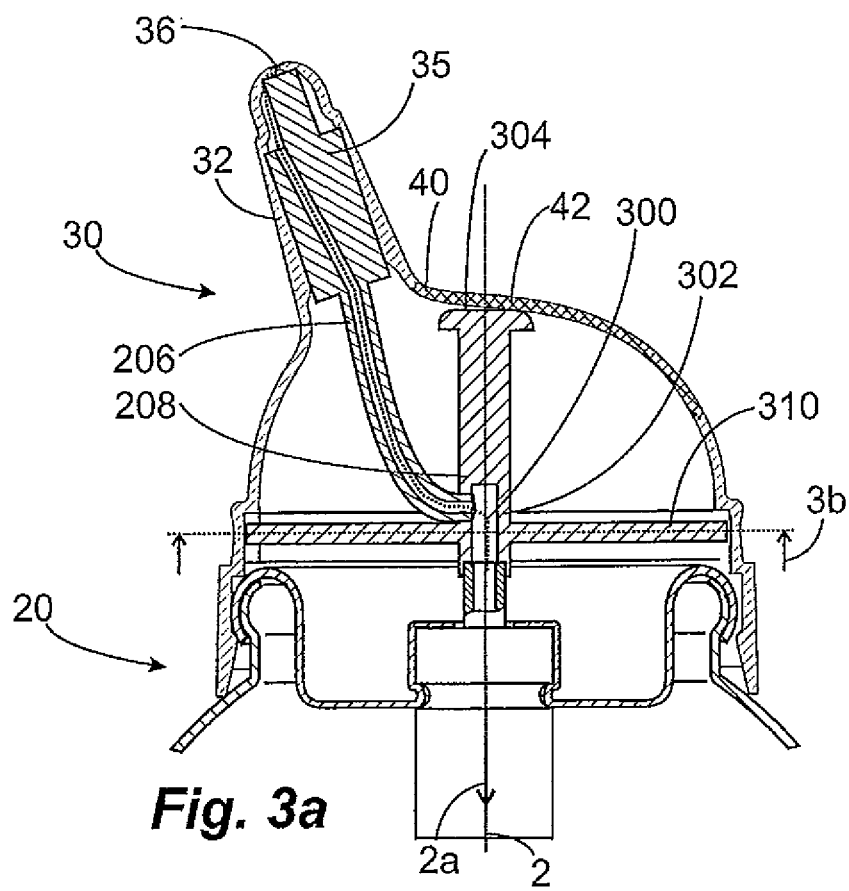
Figure 3B:
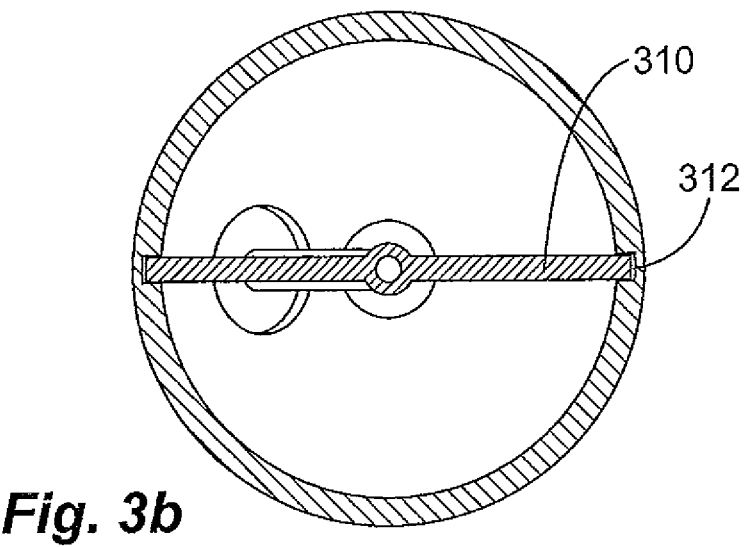

The development according to FIGS. 3a and 3b provides a variant to the development of FIGS. 2a and 2b. Said variant is illustrated in a sectional side view in FIG. 3a and in a sectional view from below in FIG. 3b. In the case of said configuration, there are provided two spokes 310 which are provided integrally on the coupling piece 302 and extend radially outward. The outer ends of said spokes 310 project into inwardly pointing grooves 312 which are provided on the inside surface of the first part portion or are fixed in position in relation hereto and which extend parallel to the main extension axis 2.

As a result of the guiding, which is formed by the spokes 310 and the grooves 312, a higher level of operating reliability is ensured in operation as the risk of the coupling piece 302 being detached from the outlet connecting piece 28a is reduced. The guiding provides advantages even beforehand during the assembly of the dispenser 10 as it allows the delivery head, after assembly thereof, to be placed onto the base unit 20 without any separate alignment. As a result of the spokes, sufficiently accurate positioning of the coupling piece 302 is achievable.

Figure 4A:
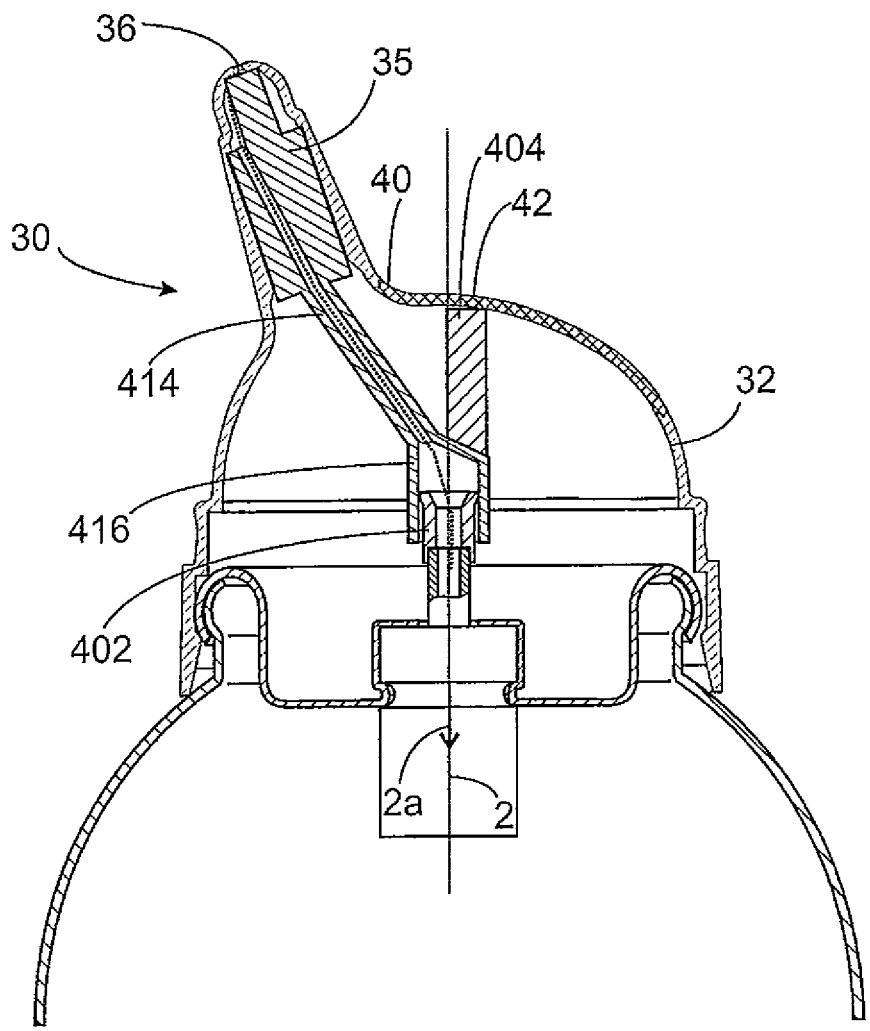
Figure 4B:
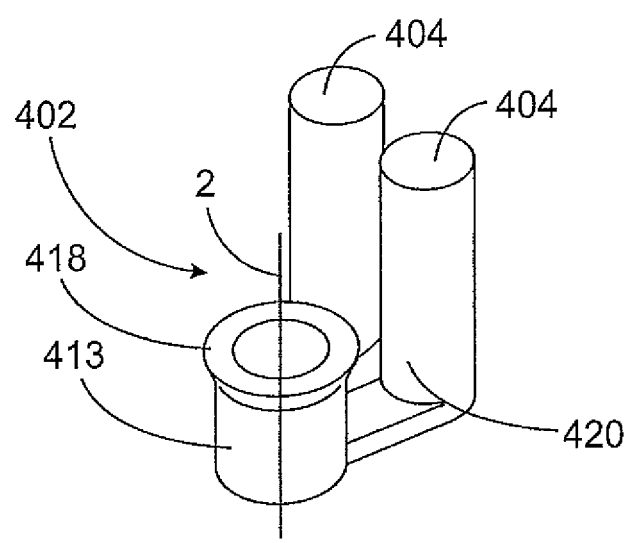

The development according to FIGS. 4a and 4b dispenses with a deformable hose, as shown in the preceding figures. Instead of which, the delivery channel 400, which connects the outlet connecting piece 28a to the delivery opening 36, is realized so as to be telescopic in a part region. In said part region, on the one hand there is a channel portion 413 of the coupling piece 402 which is placed on the outlet connecting piece 28a in a fixed manner. On the other hand there is a channel portion 416 here which is aligned in the main extension direction 2 and is connected to the insert 35 so as to be fixed in position, in the present case integrally by means of a channel portion 414. The channel portion 413 on the coupling piece side extends into the hollow cylindrical portion 416 which is fixed in position with respect to the first part portion 32, it being ensured as a result of an outwardly widening sealing lip 418 that no liquid is able to emerge in said contact region. The coupling piece 402 is shown again in FIG. 4b. It can also be seen from said figure that as an integral part of the coupling piece 402 there are provided upwardly pointing continuations 420 which are arranged eccentrically with respect to the main axis 2. Said continuations 420 extend as far as up to directly below the actuating handle 42. It is consequently possible by depressing the actuating handle 42 to press down the coupling piece 402 which is guided in the telescopic region in order also thereby to press down the outlet connecting piece 28a. The delivery operation is brought about as a result. The liquid flows through the telescopic portion to the delivery opening 36.

Figure 5A:
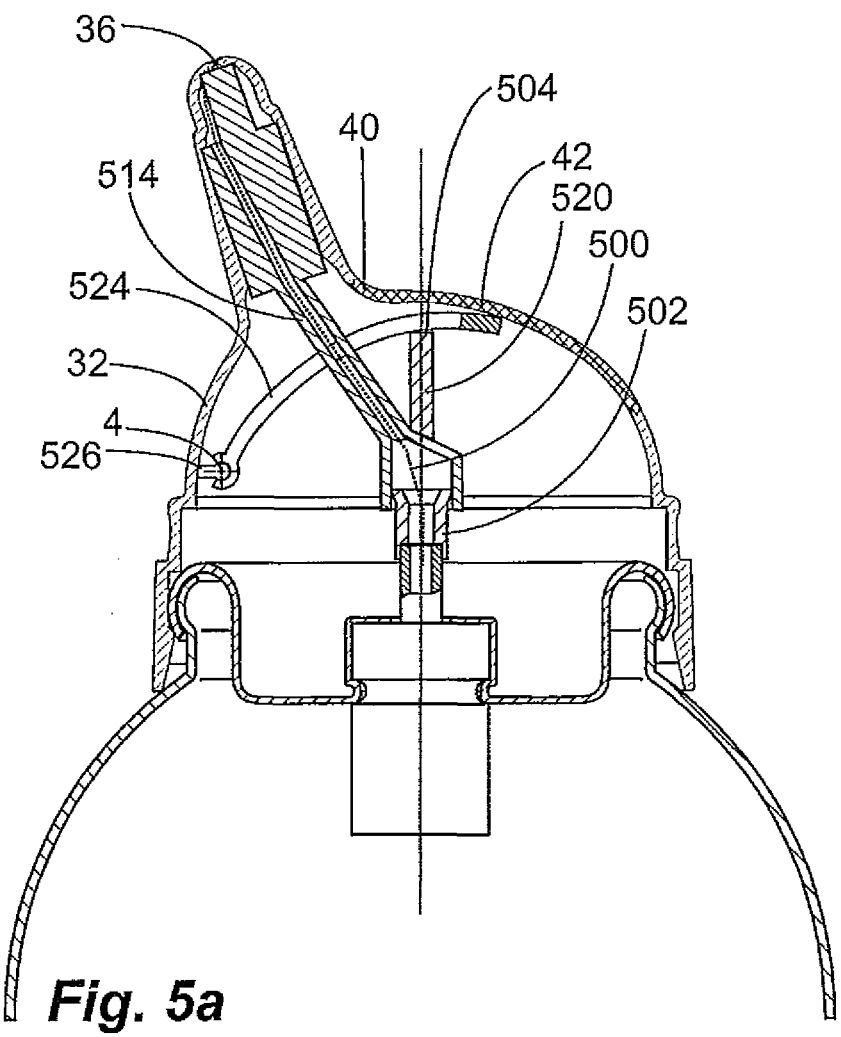
Figure 5B:
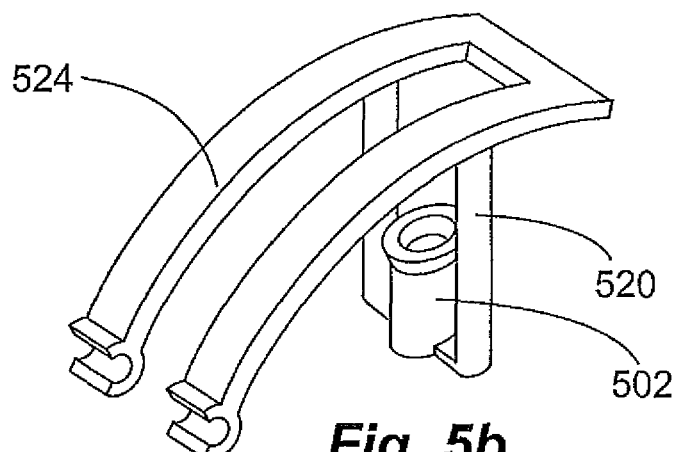

The development of FIGS. 5a and 5b is extensively similar to the development of FIGS. 4a and 4b. However, in this case it is provided that a depressing of the actuating handle 42 does not act directly on the coupling piece 502. Instead of which, there is provided an intermediate lever 524 which is mounted so as to be pivotable about a pivot axis 4 which is fixed in position with respect to the first part portion 32. Said pivot lever 524, as soon as it has been displaced downward by means of the actuating handle 42, presses onto the end faces 504 of the continuations 520 and thus brings about the delivery operation.

Figure 6A:
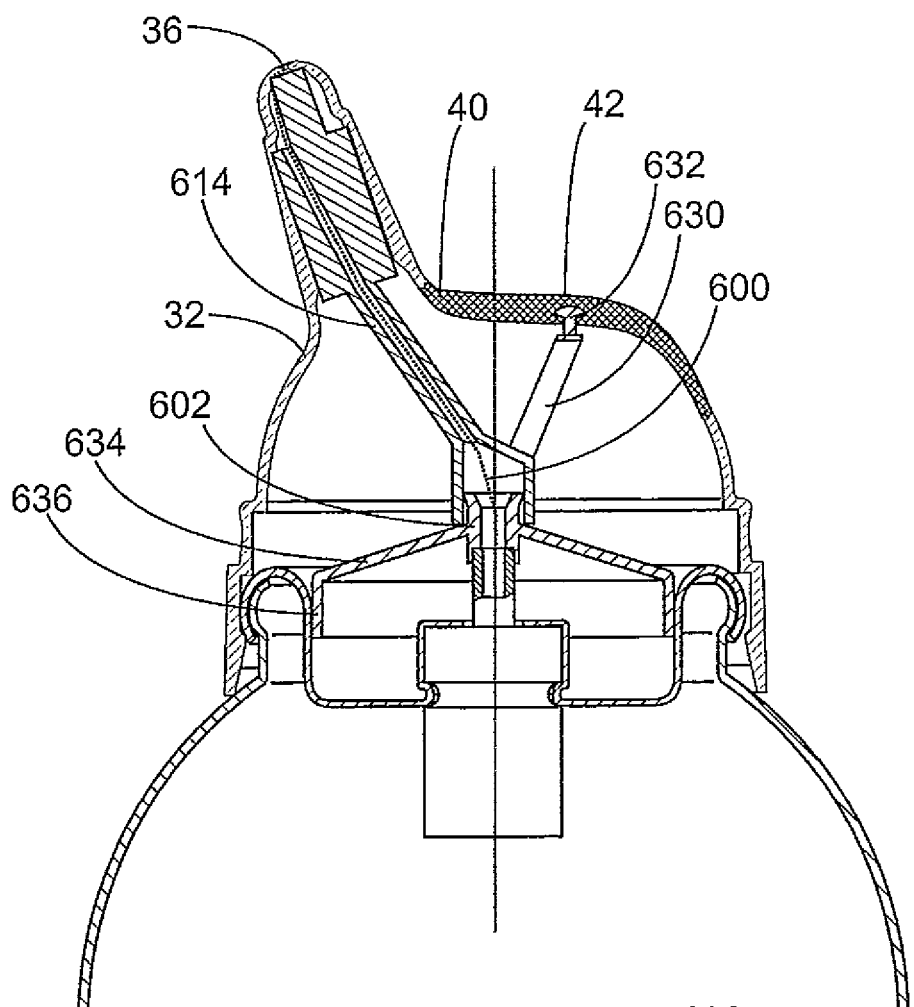
Figure 6B:
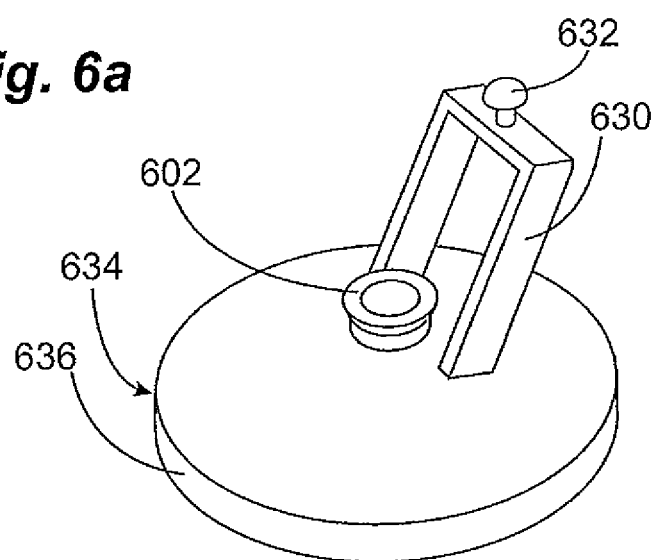

In the case of the development according to FIGS. 6a and 6b, similar to in the case of the development of FIGS. 4a and 4b, the actuating handle acts on the coupling piece 602 without the connection of a pivot lever in between. For this purpose, there is provided on the coupling piece 602 an actuating continuation 630 which extends to the actuating handle 42, on the distal end of which a mushroom-shaped widening 632 is attached. Said widening is inserted in a recess on the inside surface of the actuating handle 42. Consequently, even prior to attaching the delivery head 30 on the base unit 20, there is provided an at least approximate positioning of the coupling piece 602 which allows for a simplified assembly. As an additional characteristic in the case of the development of FIGS. 6a and 6b, it is provided that the coupling piece 602 comprises a guiding collar 634, the outside face 636 of which in the assembled state interacts with a cylindrical guiding face 26b of the crimp cover 26. As a result of said measures as well as as a result of the telescopic guiding of the coupling piece 602, which corresponds extensively to FIGS. 4a and 4b, reliable guiding of the coupling piece 602 in operation is achieved.

Figure 7A:
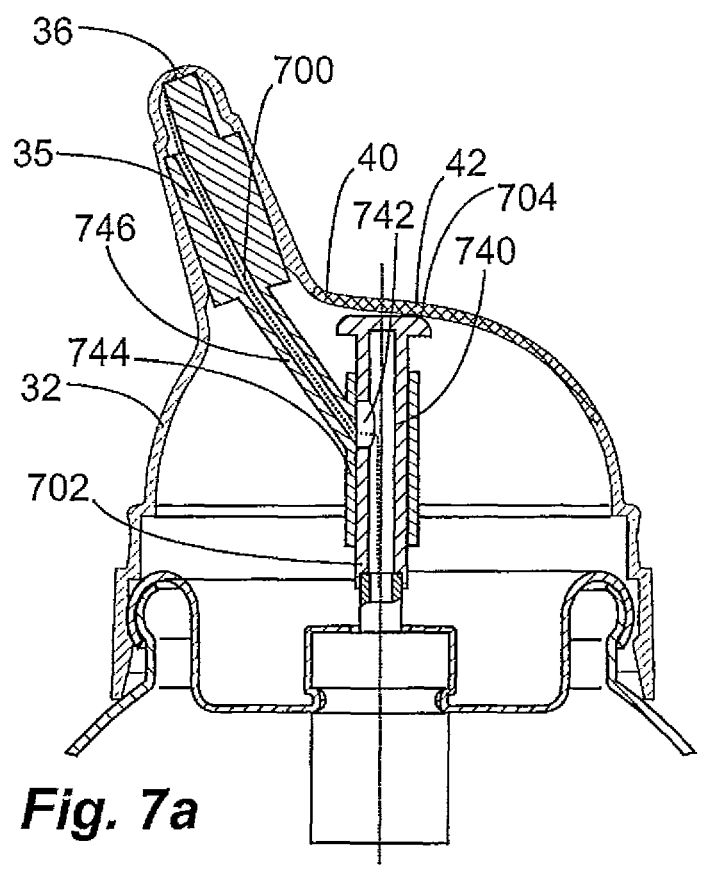
Figure 7B:
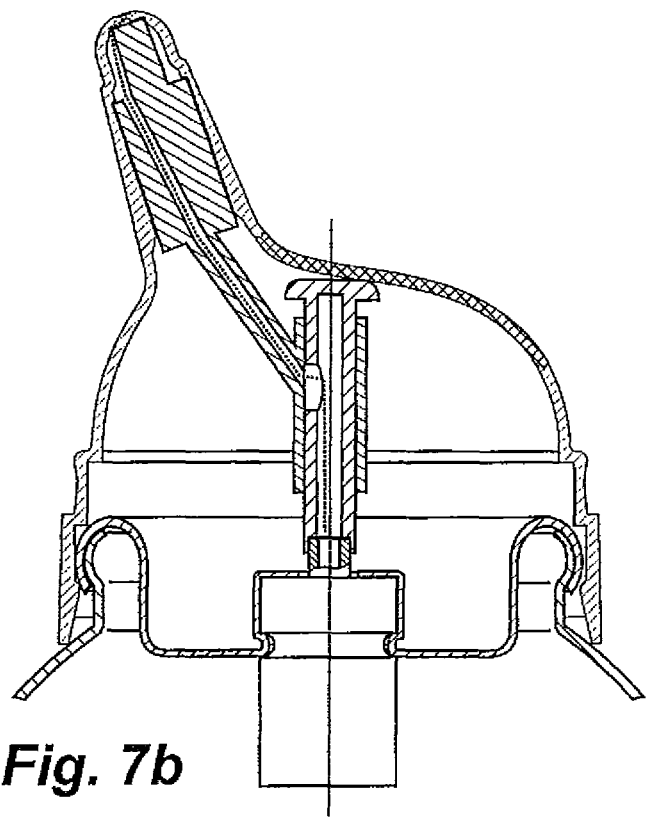

The development of FIGS. 7a and 7b is similar to the development of FIGS. 2a and 2b. Here too, there is provided a coupling piece 702 which has a pressure applying face 704 which, by depressing the actuating handle 42, is directly acted upon with force. Deviating from the development of FIGS. 2a and 2b, however, in this case no deformable hose portion is provided. Instead of which, the coupling piece 702 is provided with a radial opening 742. A sleeve 744, which is connected integrally to a tube portion 746 which extends in the direction of the delivery opening 36, is slipped onto the cylindrical outside face of the coupling piece 702. The openings 742 and the tube portion are in alignment with one another at least in phases during the delivery. As FIGS. 7a and 7b illustrate, as a result of the size of the opening 742 it is even ensured in the present case that from the non-actuated state of FIG. 7a as far as up to the actuated state of FIG. 7b, the opening 742 and the end of the tube portion 746 pointing in the direction of the coupling piece are in alignment with one another. The delivery operation can consequently be brought about as a result of pressing down the coupling piece 702. Without a deformable part per se with the exception of the second part portion 40, a permanent channel connection between the outlet connecting piece 28a and the delivery opening 36 is created along the delivery channel 700.

Figure 8:
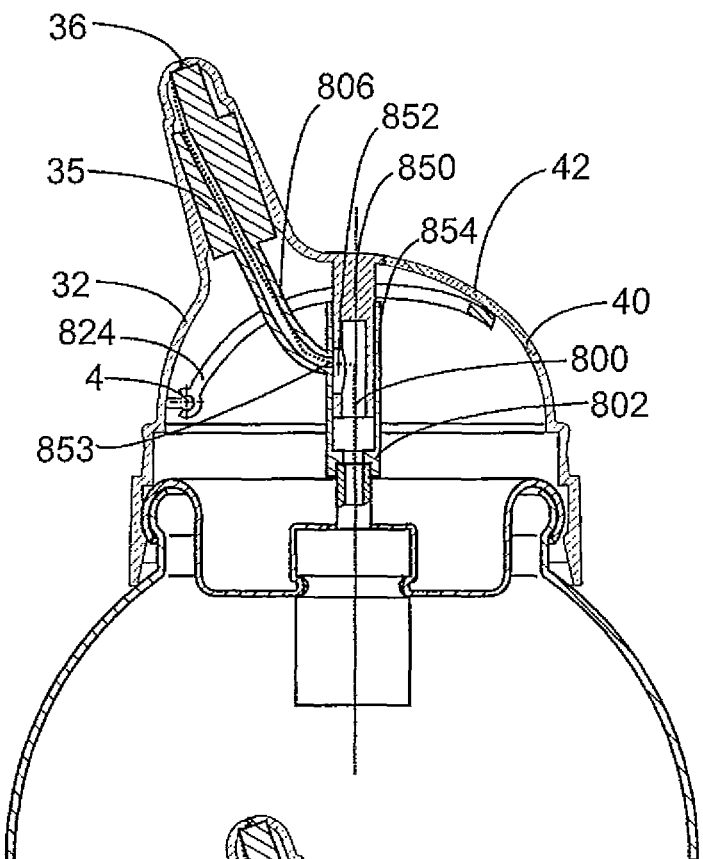

The development of FIG. 8 has affinity with the development of FIGS. 7a and 7b. In this case also, there is provided displacability of a sleeve 854 in relation to an inside tube 850, once again, openings 852, 853 being provided which are matched to one another in such a manner that both in the non-actuated and in the actuated state the delivery channel 800 between the outlet connecting piece 28a and the delivery opening 36 remains permanently open. Deviating from the development of FIGS. 7a and 7b, the inside tube 850, however, is part of the first part portion 32 of the delivery head 30 which is immobile in relation to the pressure container 24. The sleeve 854, in contrast, is part of the coupling piece 802. As the sleeve 850 is consequently movable in relation to the first part portion 32, the connection to the insert 35 is created once again by a flexible tube portion 806. Similar to the development of FIGS. 5a and 5b, the coupling piece 802 is acted upon with force not directly by means of the actuating handle 42, but by means of a pivot lever 824 which is pivotally mounted on the first part portion 32 so as to be pivotable about a pivot axis 4. In the present case, this is in particular owing to the fact that the actuating handle 42 should be arranged offset in relation to the main extension axis 2 on account of the inside tube 850 which is in alignment with the outlet connecting piece 28a.

In the case of a variant (not shown) to the embodiment of FIG. 8, the portion 852 is not realized as a tube and does not serve for guiding the liquid, but serves instead exclusively for guiding the sleeve 854. In such a case, the hose portion 806 opens out further down into the coupling piece 802. Such a configuration, where a type of continuation or bolt which extends in the direction of displacement of the outlet connecting piece and consequently can guide a pressure member as a result of the application of force of the outlet connecting piece, is also deemed as an advantageous configuration.

Figure 9:
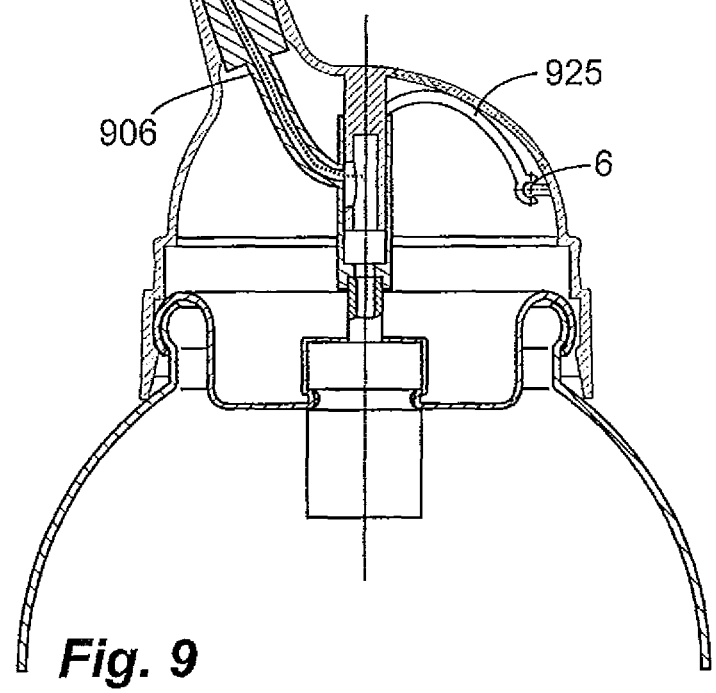

The development of FIG. 9 shows a development which is very similar to the development of FIG. 8. However, the pivot lever 925 in this case is pivotable about a pivot axis 6 on the opposite side. This allows it to utilize a simple pivot lever, instead of a divided lever in the manner of FIG. 5b, as it does not have to engage around the hose 906.

In the case of the development of FIGS. 10a to 10c, once again there is provided a lever 1024 which is pivotable about a pivot axis 4 and reaches as far as below the actuating handle 42 and as a result is able to be pivoted by pressing down the actuating handle 42 in a deforming manner. As can be seen in particular from FIG. 10b, said lever is realized integrally with the coupling piece 1002 by means of bridges 1058. A connecting hose 1006 and an insert that projects into the applicator 34 are also connected integrally thereto. The delivery head 30 consequently consists only of three components. The integral configuration of the pivot lever 1024 with the coupling piece 1002 does result in said coupling piece being pivoted to a small extent when the actuating handle 42 is actuated, this is, however, of no disadvantageous consequence on account of the pivot angle of only a few degrees.

Figure 10C:
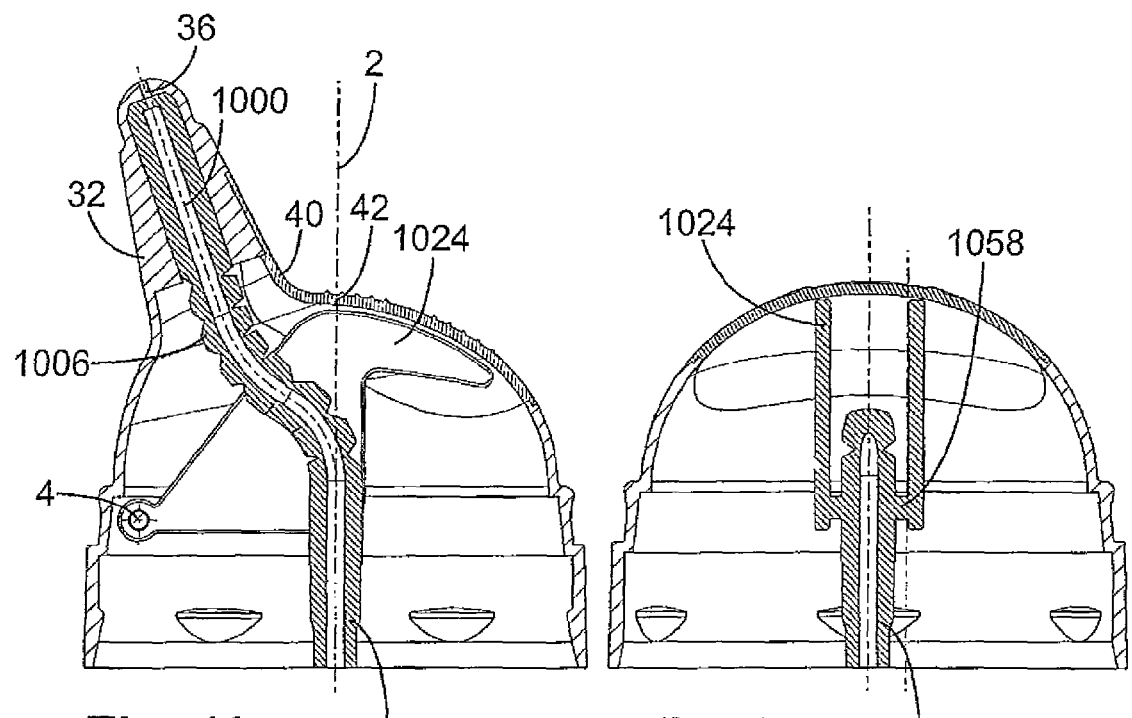
Figure 10C:
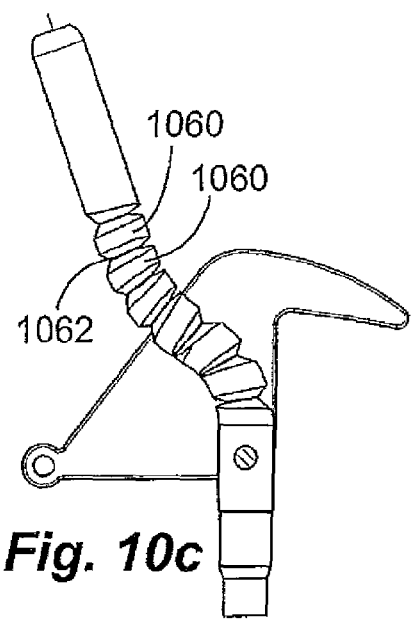

A characteristic of the development of FIGS. 10a to 10c is also the development of the hose portion 1006. Said hose portion does not have a uniform cross section, but has segments 1060 which are separated from one another by circumferential grooves 1062. The grooves 1062 result in the manner that can be taken in particular from FIG. 10a in the flexibility of the hose 1006 being limited. As soon as two segments 1060, which are separated in relation to one another by a groove 1062, directly abut against one another in the region of the groove lying in between, no continued movement is effected in said region of the hose portion 1006. Instead, a further application of force onto the hose portion 1006 will result in deformation taking place initially in the region of adjacent segments. As a result, the hose portion 1006 is prevented from buckling, as a result of which the liquid channel 1000 between the coupling piece 1002 and the outlet opening 36 could be closed.

Figure 11A:
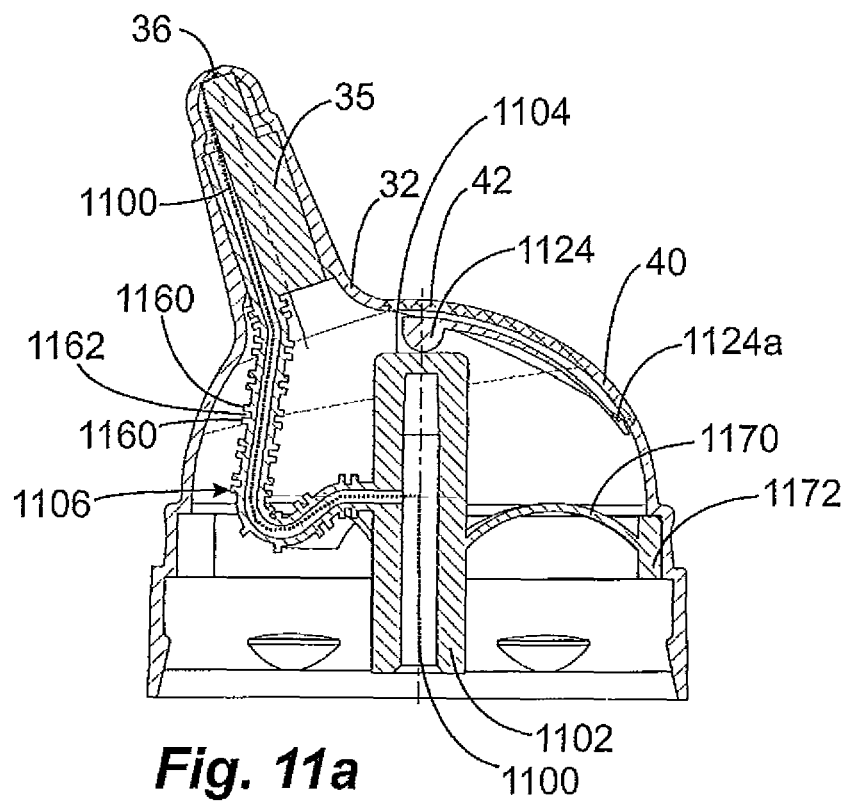
Figure 11B:
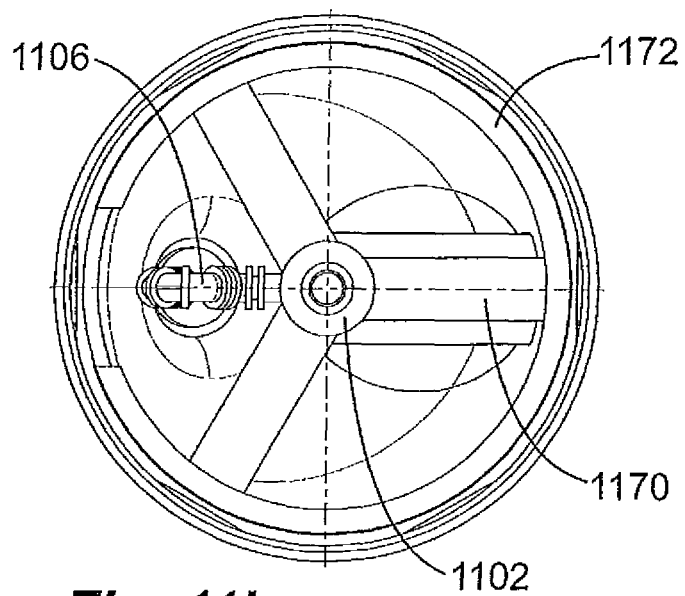

In the case of the development of FIGS. 11a and 11b, once again there is provided a coupling piece 1102 which is connected to the fill body 35 by means of a deformable hose portion 1106. The coupling piece is displaceable downward by means of a pivot lever 1124, the pivot lever 1124 being an integral part of the first part portion 32 of the delivery head 30. However, it is movable in relation to the other parts of the first part portion as a result of a thin-walled region 1124a. The application of force of the pivot lever 1106 is effected once again by means of the actuating handle 42. A characteristic of the development of FIGS. 11a and 11b is in particular the development of the hose portion 1106. Said hose portion comprises a plurality of outside collars 1060 which are spaced apart from one another and which prevent the buckling of the hose portion 1106 in a similar manner to as is given in the case of the development of FIGS. 10a to 10c.

A further characteristic of the development of FIGS. 11a and 11b is that for positioning or guiding the coupling piece 1100 a total of three deformable spokes 1170, which are integrally molded at the opposite end on a ring body 1172, are integrally molded on the coupling piece 1102. Said ring body 1172 is inserted fixed in position into the first part portion 32 of the delivery head 30 and is fixed there by means of a clamping connection in a manner not shown in any more detail. The deformable spokes 1170 cause the coupling portion 1102 to be guided. In addition, they provide a positioning aid which is advantageous when placing the delivery head 30 onto the base unit 20.

Figure 12A:
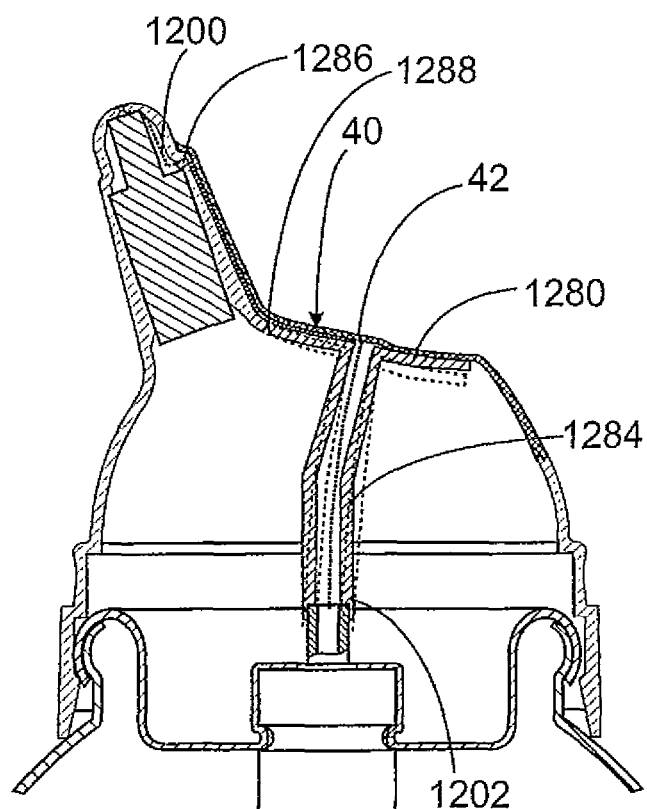
Figure 12B:
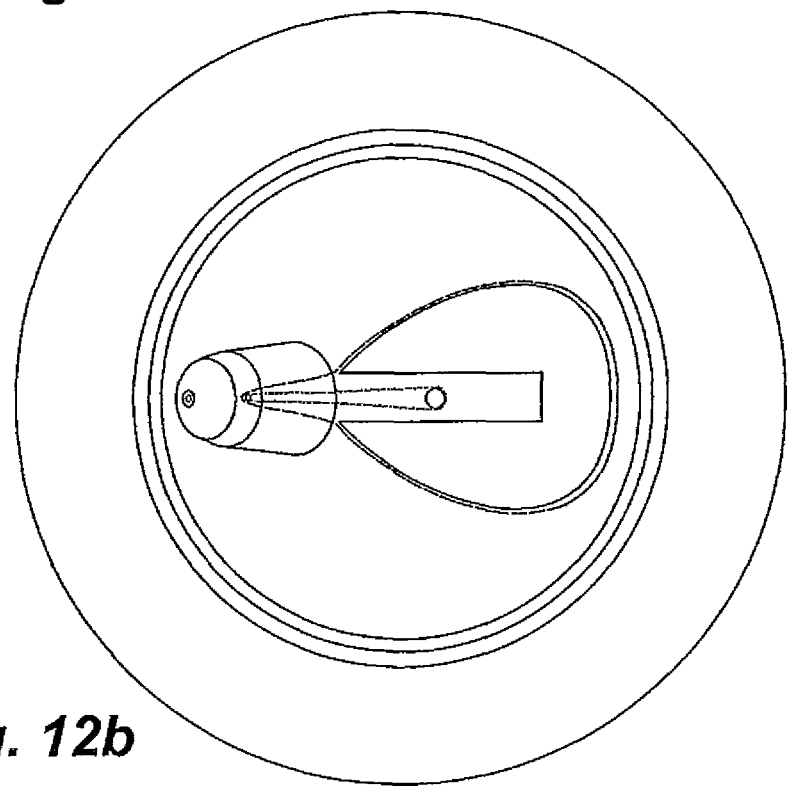

The development of FIGS. 12a and 12b differs from the preceding embodiments in that the coupling piece 1202 is integrally connected to the first part portion 32 of the delivery head 30. However, there is provided a film hinge 1288 between an outside portion 1280, which includes the coupling piece 1202, and the surrounding parts of the first part portion 32, as a result of which pivoting mobility of the portion 1280 is achieved. In the region of the portion 1280, an outside surface of the delivery head 30 is once again formed by a second part portion 40 which is applied using the two-component injection molding method. In FIG. 12b, the region covered by said soft plastics material of the second part portion 40 is indicated by the broken lines. The liquid path extends from the coupling piece 1202 as far as up to a top-side end of the portion 1284. From here, the delivery channel 1200 extends between the integral part, which forms the first part portion 32 and the portion 1202, on the one hand, and the inside surface of the second part portion 40 on the other hand. The liquid path extends here accordingly as it were on the outside surface of the delivery head. The medium can pass back into the applicator 34 through an opening 1286 which penetrates the part portion 32 at the end of said portion and can consequently flow to the delivery opening 36.

The characteristic in the case of said configuration lies consequently in particular in that a portion of the delivery channel 1200 is defined by the two plastics material parts 1280, 40 together. Along with the fact that a delivery head is consequently realizable with particularly few parts, this also results in the delivery operation being ascertainable haptically to the user, whose finger rests on the actuating handle 42.

The embodiments shown are heavily schematized for better understanding. In part they are worthy of improvement with regard to cost-efficient production. Adapting the respective parts which serve for simplified producibility in general and for improved ability for removal from the injection molding molds especially, is realizable in a simple manner by the expert.

The invention claimed is:

1. A dispenser for the delivery of liquid media, said dispenser comprising:
a base unit comprising:
a media storage unit for storing a medium; and
an outlet connecting piece movable in relation to the media storage unit in order, as a result, to cause a delivery of medium in the direction of a delivery head through the outlet connecting piece;
a delivery head comprising:
a delivery opening through which the medium escapes into an atmosphere surrounding the dispenser;
a delivery channel, at a first end of which is provided a coupling piece for coupling to the outlet connecting piece and a second end of which is connected to the delivery opening, the delivery channel between the outlet connecting piece and the delivery opening being formed at least in part by a telescopic channel region;
a first part portion including the delivery opening and including a fastening device by which the first part portion and the delivery opening are fastened in a non-movable fixed position with respect to the media storage unit on the base unit; and
a second part portion which is movable in relation to the first part portion and comprises an actuating handle operatively coupled with the coupling piece such that a displacement of the actuating handle relative to the first part portion leads to a displacement of the coupling piece in relation to the first part portion.

2. The dispenser as claimed in claim 1, wherein the media storage unit is configured for storing over-pressurized medium and/or is filled with over-pressurized medium, and the outlet connecting piece is connected to an outlet valve provided in the base unit such that a displacement of the outlet connecting piece in relation to the media storage unit leads to opening of the outlet valve.

3. The dispenser as claimed in claim 1, further including a cover disposed to close a cylindrical outside wall of the base unit at an end thereof, the cover being disposed on a side of the base unit facing the delivery head, wherein said cover defines a guiding face on which at least one guiding portion connected to the coupling piece is slidingly movable.

4. The dispenser as claimed in claim 1, further including a pivot lever mounted so as to be pivotable on the first part portion and pivotable in relation to the first part portion as a result of displacement of the second part portion, wherein the pivot lever is operatively coupled with the coupling piece such that the coupling piece is displaceable in relation to the first part portion as a result of a pivoting movement of the pivot lever.

5. The dispenser as claimed in claim 1, wherein the second part portion consists at least in part of an elastically deformable material to permit movement of the actuating handle in relation to the first part portion.

6. The dispenser as claimed in claim 5, further including a fastening portion fixed in position in relation to the coupling piece and connected in a non-positive locking, positive locking or positively bonded manner to the elastically deformable material of the second part portion.

7. The dispenser as claimed in claim 1, wherein the coupling piece has at least one pressing face acted upon with force indirectly or directly by the actuating handle in order to bring about the displacement of the outlet connecting piece in relation to the media storage unit, wherein:
the at least one pressing face is radially offset from the outlet connecting piece; or
the at least one pressing face is aligned with the outlet connecting piece and the delivery channel is deflected in a region of the coupling piece and below said pressing face.

8. The dispenser as claimed in claim 1, wherein the delivery channel in the telescopic channel region is formed by first and second channel members disposed in coaxial and telescoping relation with one another, the first channel member being non-movable relative to the first part portion and communicating with the delivery opening and the second channel member being telescopingly, slidingly and coaxially movable relative to the first channel member and movable relative to the first part portion to displace the outlet connecting piece relative to the media storage unit, the outlet connecting piece communicating with the delivery opening through the first and second channel members.

9. The dispenser as claimed in claim 8, wherein the second channel member forms part of the coupling piece.

10. The dispenser as claimed in claim 1, wherein the first part portion and the delivery opening are non-movable relative to the media storage unit during displacement of the actuating handle.

11. A dispenser for the delivery of a liquid media, said dispenser comprising:
a base unit comprising:
a storage unit configured for storing a liquid medium therein; and
a connecting piece movably mounted in relation to said storage unit to cause a delivery of medium through a fluid channel defined in said connecting piece;
a delivery head comprising:
a first portion defining a delivery opening through which medium in said storage unit is discharged into an atmosphere surrounding said dispenser, said first portion being fixedly fastened to said storage unit such that said first portion and said delivery opening thereof are non-movable relative to said storage unit;
a coupling element connected to said connecting piece and fluidly interconnecting said connecting piece with said delivery opening;
a second portion including an actuator operatively connected to said coupling element such that a displacement of said actuator relative to said first portion causes a displacement of said coupling element in relation to said first portion which, in turn, causes a corresponding displacement of said connecting piece and delivery of medium through said connecting piece and discharge thereof from said delivery opening, said first portion and said delivery opening thereof being non-movable relative to said storage unit during displacement of said connecting piece; and
first and second channel members disposed in telescoping and coaxial sliding relation with one another, said first channel member being non-movable relative to said first portion and communicating with said delivery opening and said second channel member being telescopingly, slidingly and coaxially movable relative to said first channel member and movable relative to said first portion to displace said connecting piece relative to said storage unit, said connecting piece communicating with said delivery opening through said first and second channel members.

12. The dispenser as claimed in claim 11, wherein said second channel member forms part of said coupling element.

* * * * *